United States Patent
Koo et al.

(10) Patent No.: US 10,444,123 B2
(45) Date of Patent: Oct. 15, 2019

(54) **VOLATILE ORGANIC COMPOUNDS (VOCS) FOR THE DIAGNOSIS OF *CLOSTRIDIUM DIFFICILE*-ASSOCIATED DIARRHEA (CDAD)**

(71) Applicant: The Brigham and Women s Hospital, Inc., Boston, MA (US)

(72) Inventors: Sophia Koo, Brookline, MA (US); Lindsey Robert Baden, Brookline, MA (US); Francisco M. Marty, Chestnut Hill, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 15/500,377

(22) PCT Filed: Aug. 3, 2015

(86) PCT No.: PCT/US2015/043410
§ 371 (c)(1),
(2) Date: Jan. 30, 2017

(87) PCT Pub. No.: WO2016/019371
PCT Pub. Date: Feb. 4, 2016

(65) Prior Publication Data
US 2017/0227429 A1    Aug. 10, 2017

Related U.S. Application Data

(60) Provisional application No. 62/032,226, filed on Aug. 1, 2014.

(51) Int. Cl.
| | | |
|---|---|---|
| *A61K 39/07* | (2006.01) | |
| *A61K 39/02* | (2006.01) | |
| *A61K 39/00* | (2006.01) | |
| *G01N 1/22* | (2006.01) | |
| *C12Q 1/04* | (2006.01) | |
| *G01N 33/497* | (2006.01) | |

(52) U.S. Cl.
CPC ............ *G01N 1/2214* (2013.01); *C12Q 1/04* (2013.01); *G01N 1/22* (2013.01); *G01N 33/497* (2013.01); *G01N 2033/4975* (2013.01); *G01N 2333/33* (2013.01)

(58) Field of Classification Search
CPC ........... G01N 1/00; G01N 1/22; G01N 1/2226
USPC ..... 424/93.41, 234.1; 436/63, 161, 174, 181
See application file for complete search history.

(56) References Cited

U.S. PATENT DOCUMENTS

| | | |
|---|---|---|
| 7,605,367 B2 | 10/2009 | Miller et al. |
| 2006/0008918 A1* | 1/2006 | Probert .............. G01N 33/497 436/106 |
| 2007/0003996 A1 | 1/2007 | Hitt et al. |
| 2009/0078865 A1 | 3/2009 | Zapata et al. |
| 2010/0291617 A1 | 11/2010 | Trevejo et al. |
| 2012/0309048 A1 | 12/2012 | Ratcliffe et al. |
| 2013/0052640 A1 | 2/2013 | Boone et al. |
| 2013/0129695 A1 | 5/2013 | Blount |
| 2013/0168548 A1 | 7/2013 | Wang et al. |

FOREIGN PATENT DOCUMENTS

WO    2011/151619    12/2011

OTHER PUBLICATIONS

Antharam et al., "Intestinal dysbiosis and depletion of butyrogenic bacteria in Clostridium difficile infection and nosocomial diarrhea," Journal of Clinical Microbiology, Sep. 2013, 51: 2884-92.
Backhed et al., "Host-bacterial mutualism in the human intestine," Science, Mar. 2005, 307: 1915-20.
Barbut et al., "Does a rapid diagnosis of Clostridium difficile infection impact on quality of patient management?," Clinical Microbiology and Infection, Feb. 2014, 20: 136-44.
Bartlett and Gerding, "Clinical recognition and diagnosis of Clostridium difficile infection," Clinical Infectious Diseases, Jan. 2008, 46 Suppl 1: S12-8.
Bartlett et al., "Antibiotic-associated pseudomembranous colitis due to toxin-producing clostridia," The New England Journal of Medicine, Mar. 1978, 298: 531-4.
Bartlett et al., "Clindamycin-Associated Colitis Due to a Toxin-Producing Species of *Clostridium* in Hamsters," The Journal of Infectious Diseases Nov. 1977, 136: 701-5.
Bobulsky et al., "Clostridium difficile Skin Contamination in Patients with C. difficile-Associated Disease," Clinical Infectious Diseases, Feb. 2008, 46: 447-50.
Bomers et al., "A detection dog to identify patients with Clostridium difficile infection during a hospital outbreak," The Journal of Infection, Nov. 2014, 69(5):456-61.
Bomers et al., "Using a Dog's Superior Olfactory Sensitivity to Identify Clostridium difficile in Stools and Patients: Proof of Principle Study," BMJ, 2012, 345: e7396.
Brecher et al., "Laboratory Diagnosis of Clostridium difficile Infections: There is Light at the End of the Colon," Clinical Infectious Diseases, 2013, 57: 1175-81.
Britton and Young, "Role of the Intestinal Microbiota in Resistance to Colonization by Clostridium difficile," Gastroenterology, 2014, 146: 1547-53.
Buffie and Pamer, "Microbiota-mediated colonization resistance against intestinal pathogens," Nature Reviews Immunology, Nov. 2013, 13: 790-801.
Buffie et al., "Profound Alterations of Intestinal Microbiota following a Single Dose of Clindamycin Results in Sustained Susceptibility to Clostridium difficile-Induced Colitis," Infection and Immunity, Jan. 2012, 80: 62-73.

(Continued)

*Primary Examiner* — Rodney P Swartz
(74) *Attorney, Agent, or Firm* — Fish & Richardson P.C.

(57) ABSTRACT

Methods for diagnosing, treating, and monitoring the treatment of *Clostridium difficile* infections (CDI), e.g., *Clostridium difficile*-Associated Diarrhea (CDAD). The methods can include detecting the presence of one or more volatile organic compounds (VOCs) in a sample from ambient air or stool sample from subjects suspected of having a CDI, e.g., CDAD.

16 Claims, 1 Drawing Sheet

(56) References Cited

OTHER PUBLICATIONS

Burdette and Bernstein, "Does the Nose Know? The Odiferous Diagnosis of Clostridium difficile-Associated Diarrhea," Clinical Infectious Diseases, Apr. 2007, 44: 1142.
Chang et al., "Decreased diversity of the fecal Microbiome in recurrent Clostridium difficile-associated diarrhea," The Journal of Infectious Diseases, Feb. 2008, 197: 435-8.
Chang et al., "Neutralization of Clostridium difficile toxin by Clostridium sordellii antitoxins," Infection and Immunity, Nov. 1978, 22: 418-22.
Chitnis et al., "Epidemiology of Community-Associated Clostridium difficile Infection, 2009 Through 2011," JAMA Internal Medicine, Jul. 2013, 173: 1359-67.
Cohen et al., "Clinical Practice Guidelines for Clostridium difficile Infection in Adults: 2010 Update by the Society for Healthcare Epidemiology of America (SHEA) and the Infectious Diseases Society of America (IDSA)," Infection Control and Hospital Epidemiology, May 2010, 31: 431-55.
Crobach et al., "European Society of Clinical Microbiology and Infectious Diseases (ESCMID): Data review and recommendations for diagnosing Clostridium difficile-infection (CDI)," Clinical Microbiology and Infection, Dec. 2009, 15: 1053-66.
Davis et al., "Fabrication and Characterization of Laser Micromachined Hollow Microneedles," In: 12th International Conference on Transducers, Solid-State Sensors, Actuators and Microsystems; 2003, 1435-1438.
Dethlefsen et al., "The Pervasive Effects of an Antibiotic on the Human Gut Microbiota, as Revealed by Deep 16S rRNA Sequencing," PLoS Biology, Nov. 2008, 6: e280.
Dial et al., "Use of Gastric Acid-Suppressive Agents and the Risk of Community-Acquired Clostridium difficile-Associated Disease," JAMA, Dec. 2005, 294: 2989-95.
Draft Guidance for Industry and Food and Drug Administration Staff—Establishing the Performance Characteristics of In Vitro Diagnostic Devices for the Detection of Clostridium difficile, U.S. Department of Health and Human Services Food and Drug Administration Center for Devices and Radiological Health, Nov. 2010, 21 pages.
Dubberke et al., "Strategies to prevent Clostridium difficile infections in acute care hospitals: 2014 Update," Infection Control and Hospital Epidemiology, Jun. 2014, 35: 628-45.
Dubberke, "Clostridium difficile infection: the scope of the problem," Journal of Hospital Medicine, Mar. 2012, 7 Suppl 3: S1-4.
Dupuy et al., "Regulated transcription of Clostridium difficile toxin genes," Molecular Microbiology, Jan. 1998, 27: 107-20.
Eastwood et al., "Comparison of Nine Commercially Available Clostridium difficile Toxin Detection Assays, a Real-Time PCR Assay for C. difficile tcdB, and a Glutamate Dehydrogenase Detection Assay to Cytotoxin Testing and Cytotoxigenic Culture Methods," Journal of Clinical Microbiology, 2009, 47: 3211-3217.
Eckburg et al., "Diversity of the human intestinal microbial flora," Science, Jun. 2005, 308: 1635-8.
Fenner et al., "Rapid and Reliable Diagnostic Algorithm for Detection of Clostridium difficile," Journal of Clinical Microbiology, Jan. 2008, 46: 328-30.
Fong et al., "Automated peak detection and matching algorithm for gas chromatography-differential mobility spectrometry," Anal Chem, Mar. 2011, 83:1537-46.
Franzosa et al., "Relating the metatranscriptome and metagenome of the human gut," PNAS, Jun. 2014, 111: E2329-38.
Freeman et al., "The changing epidemiology of Clostridium difficile infections," Clinical Microbiology Reviews, Jul. 2010, 23: 529-49.
Frenz and McIntyre, "Reducing delays in the diagnosis and treatment of Clostridium difficile diarrhea," QJM, 2003, 96: 579-582.
Fukuda et al., "Acetate-producing bifidobacteria protect the host from enteropathogenic infection via carbohydrate transporters," Gut Microbes, Sep./Oct. 2012, 3: 449-54.

Fukuda et al., "Bifidobacteria can protect from enteropathogenic infection through production of acetate," Nature, Jan. 2011, 469: 543-7.
Garner et al., "Volatile Organic Compounds from Feces and Their Potential for Diagnosis of Gastrointestinal Disease," FASEB J, 2007, 21: 1675-1688.
Gill et al., "Metagenomic Analysis of the Human Distal Gut Microbiome," Science, 2006, 312: 1355-9.
Grein et al., "Comparison of testing approaches for Clostridium difficile infection at a large community hospital," Clinical Microbiology and Infection, Jan. 2014, 20: 65-9.
Hensgens et al., "All-Cause and Disease-Specific Mortality in Hospitalized Patients With Clostridium difficile Infection: A Multicenter Cohort Study," Clinical Infectious Diseases, 2013, 56: 1108-16.
Howerton et al., "A New Strategy for the Prevention of Clostridium difficile Infection," The Journal of Infectious Diseases, 2013, 207: 1498-1504.
Huttenhower et al., "Structure, Function and Diversity of the Healthy Human Microbiome," Nature, Jun. 2012, 486: 207-214.
Hutton et al., "Small animal models for the study of Clostridium difficile disease pathogenesis," FEMS Microbiol Lett., Mar. 2014, 352(2):140-9.
International Preliminary Report on Patentability in International Application No. PCT/US2015/043410, dated Feb. 7, 2017, 9 pages.
Johansen et al., "Clostridium difficile Associated Diarrhoea: How Good Are Nurses at Identifying the Disease?," Age and Ageing, Nov. 2002, 31: 487-8.
Kanu and Hill Jr., "Ion mobility spectrometry detection for gas chromatography," J Chromatogr A, Jan. 2008, 1177:12-27.
Kanu et al., "Ion mobility—mass spectrometry," J Mass Spectrom 2008; 43: 1-22.
Kolakowski and Mester, "Review of applications of high-field asymmetric waveform ion mobility spectrometry (FAIMS) and differential mobility spectrometry (DMS)," Analyst, 2007, 132:842-64.
Koo et al., "D-203—Stool Volatile Organic Compounds for the Diagnosis of Clostridium difficile-Associated Diarrhea," In: 54th Interscience Conference on Antimicrobial Agents and Chemotherapy, Sep. 2014, 2 pages.
Köpke, "Clostridium difficile is an Autotrophic Bacterial Pathogen," PloS One, Apr. 2013, 8: e62157.
Krebs et al., "Detection of Biological and Chemical Agents Using Differential Mobility Spectrometry (DMS) Technology," Sensors Journal, IEEE, Aug. 2005, 5(4):696-703.
Kuehn et al., "The role of toxin A and toxin B in Clostridium difficile infection," Nature, Oct. 2010, 467: 711-3.
Kundrapu et al., "Easily Modified Factors Contribute to Delays in Diagnosis of Clostridium difficile Infection: a Cohort Study and Intervention," Journal of Clinical Microbiology, Jul. 2013, 51: 2365-70.
Kwok et al., "Risk of Clostridium difficile Infection With Acid Suppressing Drugs and Antibiotics: Meta-Analysis," The American Journal of Gastroenterology, 2012, 107: 1011-9.
Longtin et al., "Impact of the Type of Diagnostic Assay on Clostridium difficile Infection and Complication Rates in a Mandatory Reporting Program," Clinical Infectious Diseases, 2013, 56: 67-73.
Loo et al., "Host and pathogen factors for Clostridium difficile infection and colonization," The New England Journal of Medicine, Nov. 2011, 365: 1693-703.
Luong et al., Gas Chromatography with State-of-the-Art Micromachined Differential Mobility Detection: Operation and Industrial ApplicationsJ Chromatogr Sci, May/Jun. 2006, 44:276-286.
Lyras et al., "Toxin B is essential for virulence of Clostridium difficile," Nature, Apr. 2009, 458: 1176-9.
McDonald et al., "Vital signs: preventing Clostridium difficile infections," Morbidity and Mortality Weekly Report, Mar. 2012, 61: 157-62.
McFarland et al., "Nosocomial Acquisition of Clostridium difficile Infection," The New England Journal of Medicine, Jan. 1989, 320: 204-10.

(56) References Cited

OTHER PUBLICATIONS

Miller et al., "A MEMS radio-frequency ion mobility spectrometer for chemical vapor detection," Sensors and Actuators, 2001, 91: 307-318.
Miller et al., "A novel micromachined high-field asymmetric waveform-ion mobility spectrometer," Sensors and Actuators B, 2000, 67: 300-306.
Mitchell and Gardner, "Mortality and Clostridium difficile infection: a review," Antimicrobial Resistance and Infection Control, 2012, 1: 20.
Nazarov et al., "Pressure effects in differential mobility spectrometry," Anal Chem, Nov. 2006, 78: 7697-7706.
Ng et al., "Microbiota-liberated host sugars facilitate post-antibiotic expansion of enteric pathogens," Nature, Oct. 2013, 502: 96-9.
Novak-Weekley et al., "Clostridium difficile testing in the clinical laboratory by use of multiple testing algorithms," Journal of Clinical Microbiology, Mar. 2010, 48: 889-93.
Peterfreund et al., "Succession in the gut microbiome following antibiotic and antibody therapies for Clostridium difficile," PLoS One, Oct. 2012, 7: e46966.
Peterson et al., "Laboratory testing for Clostridium difficile infection: light at the end of the tunnel," American Journal of Clinical Pathology, Sep. 2011, 136: 372-80.
Probert et al., "A Novel Method for Rapidly Diagnosing the Causes of Diarrhoea," Gut, 2004, 53: 58-61.
Rao et al., "The Nose Knows Not: Poor Predictive Value of Stool Sample Odor for Detection of Clostridium difficile," Clinical Infectious Diseases, 2013, 56: 615-6.
Rea et al., "Effect of broad- and narrow-spectrum antimicrobials on Clostridium difficile and microbial diversity in a model of the distal colon," PNAS, Mar. 2011, 108 Suppl 1: 4639-44.
Reller et al., "Yield of stool culture with isolate toxin testing versus a two-step algorithm including stool toxin testing for detection of toxigenic Clostridium difficile," Journal of Clinical Microbiology, Nov. 2007, 45: 3601-5.
Scheurer, "Diagnostic and treatment delays in recurrent Clostridium difficile-associated disease," Journal of Hospital Medicine, 2008, 3: 156-9.
Schroeder et al., "Economic Evaluation of Laboratory Testing Strategies for Hospital-Associated Clostridium difficile Infection," Journal of Clinical Microbiology Feb. 2014, 52: 489-96.
Schubert et al., "Microbiome Data Distinguish Patients with Clostridium difficile Infection and Non-C. difficile-Associated Diarrhea from Healthy Controls," MBio, May/Jun. 2014, 5: e01021-14.
Seekatz and Young, "Clostridium difficile and the microbiota," The Journal of Clinical Investigation, Oct. 2014, 124(10):4182-9.
Sethi et al., "Persistence of Skin Contamination and Environmental Shedding of Clostridium difficile during and after Treatment of C. difficile Infection," Infection Control and Hospital Epidemiology, Jan. 2010, 31: 21-7.
Shnayderman et al., "Species-specific bacteria identification using differential mobility spectrometry and bioinformatics pattern recognition," Anal Chem, Sep. 2005, 77:5930-7.
Skraban et al., "Gut Microbiota Patterns Associated with Colonization of Different Clostridium difficile Ribotypes," PloS One, Feb. 2013, 8: e58005.
Song et al., "Microbiota Dynamics in Patients Treated with Fecal Microbiota Transplantation for Recurrent Clostridium difficile Infection," PLoS One, Nov. 2013, 8: e81330.
Stiemsma et al., "An antibiotic-altered microbiota provides fuel for the enteric foe," Cell Research, Jan. 2014, 24: 5-6.
Sunkesula et al., "Does Empirical Clostridium difficile Infection (CDI) Therapy Result in False-Negative CDI Diagnostic Test Results?," Clinical Infectious Diseases, 2013, 57: 494-500.
Surawicz et al., "Guidelines for diagnosis, treatment, and prevention of Clostridium difficile infections," The American Journal of Gastroenterology, Apr. 2013, 108: 478-98; quiz 499.
Theriot et al., "Antibiotic-induced shifts in the mouse gut microbiome and metabolome increase susceptibility to Clostridium difficile infection," Nature Communications, 2014, 5: 3114.
Tibshirani, "Regression Shrinkage and Selection via the Lasso," Journal of the Royal Statistical Society: Series B, 1996, 58: 267-288.
Ticehurst et al., "Effective Detection of Toxigenic Clostridium difficile by a Two-Step Algorithm Including Tests for Antigen and Cytotoxin," Journal of Clinical Microbiology, Mar. 2006, 44: 1145-9.
Tisch, and Haick, "Chemical Sensors for Breath Gas Analysis: The Latest Developments at the Breath Analysis Summit 2013," Journal of Breath Research, 2014, 8: 027103.
Vincent et al., "Reductions in intestinal Clostridiales precede the development of nosocomial Clostridium difficile infection," Microbiome, Jun. 2013, 1: 18.
Wilcox, "Overcoming barriers to effective recognition and diagnosis of Clostridium difficile infection," Clinical Microbiology and Infection, Dec. 2012, 18 (Suppl 6): 13-20.
Wilson and Perini, "Role of Competition for Nutrients in Suppression of Clostridium difficile by the Colonic Microflora," Infection and Immunity, Oct. 1988, 56: 2610-4.
Woolfenden, "Sorbent-Based Sampling Methods for Volatile and Semi-Volatile Organic Compounds in Air Part 1: Sorbent-Based Air Monitoring Options," J Chromatogr A, 2010, 1217: 2674-2684.
International Search Report and Written Opinion dated Oct. 28, 2015 in International Application No. PCT/US2015/43410, 16 pgs.

* cited by examiner

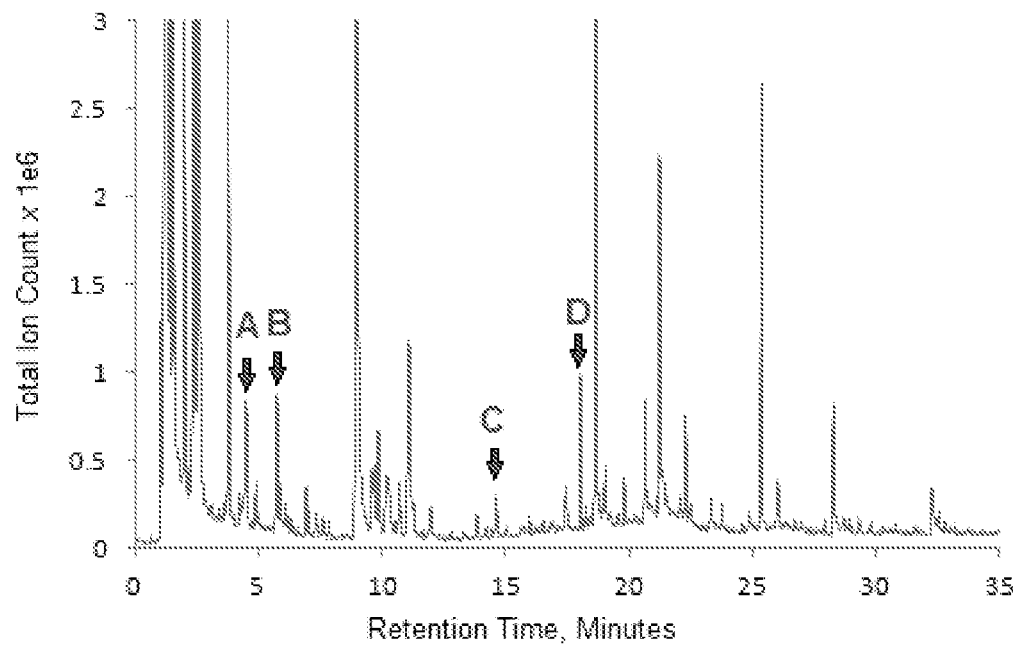

VOLATILE ORGANIC COMPOUNDS (VOCS) FOR THE DIAGNOSIS OF *CLOSTRIDIUM DIFFICILE*-ASSOCIATED DIARRHEA (CDAD)

CLAIM OF PRIORITY

This application is a § 371 National Stage Application of PCT/US2015/043410, filed Aug. 3, 2015, which claims the benefit of U.S. Provisional Application Ser. No. 62/032,226, filed on Aug. 1, 2014. The entire contents of the foregoing are incorporated herein by reference.

FEDERALLY SPONSORED RESEARCH OR DEVELOPMENT

This invention was made with Government support under Grant No. K23 AI097225 and R21 AI119692 awarded by the National Institutes of Health. The Government has certain rights in the invention.

TECHNICAL FIELD

Provided herein are methods for diagnosing, treating, and monitoring the treatment of *Clostridium difficile* infections (CDI), e.g., *Clostridium difficile*-Associated Diarrhea (CDAD). The methods can include detecting the presence of one or more volatile organic compounds (VOCs) in a sample from ambient air or stool sample from subjects suspected of having a CDI, e.g., CDAD.

BACKGROUND

*Clostridium difficile* infection (CDI) is one of the most common healthcare-associated infections (HAI) worldwide, causing substantial morbidity and mortality (Bartlett and Gerding, Clinical Infectious Diseases 2008, 46 Suppl 1, S12-8; Freeman et al., Clinical Microbiology Reviews 2010, 23, 529-49). *C. difficile* produces hardy spores, which are shed abundantly from the stool of patients with CDI, with contamination of patient skin, fomites, environmental surfaces, and hands of healthcare personnel (McFarland et al., The New England Journal of Medicine 1989, 320, 204-10; Bobulsky et al., Clinical Infectious Diseases 2008, 46, 447-50; Sethi et al., Infection Control and Hospital Epidemiology 2010, 31, 21-7). Patients acquire CDI by ingesting these ubiquitous spores, which germinate and proliferate in the intestine of individuals whose normal intestinal microbiota has been disrupted by exposure to antibiotics or proton pump inhibitors, or by weakened immunity (Bartlett and Gerding, Clinical Infectious Diseases 2008, 46 Suppl 1, S12-8; Freeman et al., Clinical Microbiology Reviews 2010, 23, 529-49; Cohen et al., Infection Control and Hospital Epidemiology 2010, 31, 431-55; Seekatz et al., The Journal of Clinical Investigation 2014, 124(10):4182-9; Britton and Young, Gastroenterology 2014, 146, 1547-53; Loo et al., The New England Journal of Medicine 2011, 365, 1693-703; Dubberke, Journal of Hospital Medicine 2012, 7 Suppl 3, S1-4; Chitnis et al., JAMA Internal Medicine 2013, 173, 1359-67; Dial et al., JAMA 2005, 294, 2989-95; Kwok et al., The American Journal of Gastroenterology 2012, 107, 1011-9). These vegetative *C. difficile* organisms elaborate exotoxins, with mucosal inflammation and injury, release of inflammatory mediators, and neutrophil recruitment (Britton and Young, Gastroenterology 2014, 146, 1547-53; Dupuy et al., Molecular Microbiology 1998, 27, 107-20; Kuehne et al., Nature 2010, 467, 711-3; Lyras, D.; O'Connor, J. R.; Howarth, P. M.; Sambol, S. P.; Carter et al., Nature 2009, 458, 1176-9). This toxin-mediated mucosal injury and host inflammatory response manifest clinically as pseudomembranous colitis with diarrhea, often accompanied by abdominal pain, fever, and leukocytosis, but may also result in a more fulminant clinical course with toxic megacolon, bowel perforation, septic shock, and death (Bartlett and Gerding, Clinical Infectious Diseases 2008, 46 Suppl 1, S12-8; Bartlett et al., The Journal of Infectious Diseases 1977, 136, 7015; Bartlett et al., The New England Journal of Medicine 1978, 298, 531-4). The attributable mortality of CDI is 5-10%, or approximately 14,000-20,000 deaths per year in the United States alone, making it one of the top 20 causes of death in individuals 65 years or older (Dubberke, Journal of Hospital Medicine 2012, 7 Suppl 3, S1-4; Dubberke et al., Infection Control and Hospital Epidemiology 2014, 35, 628-45; Hensgens et al., Clinical Infectious Diseases 2013, 56, 1108-16; Mitchell and Gardner, Antimicrobial Resistance and Infection Control 2012, 1, 20).

SUMMARY

The present invention is based, at least in part, on the identification of a volatile metabolite signature of CDI that can be used, e.g., for bedside identification of patients with CDI, allowing prompt antimicrobial treatment of patients with CDI, withholding of empiric antimicrobials in patients without CDI, and initiation of contact precaution and isolation measures to reduce the nosocomial spread of CDI.

Thus, provided herein are methods for diagnosing a subject with a *Clostridium difficile* infection (CDI), e.g., *C. difficile*-Associated Diarrhea (CDAD). The methods include obtaining a sample comprising ambient air obtained from near a subject or headspace from a stool sample suspected of comprising *C. difficile* isolated from a subject, e.g., from a subject suspected of have a *C. difficile* infection; detecting the presence in the sample of one, two, three, or four volatile organic compounds (VOCs) produced by the *C. difficile* in a sample comprising ambient air from near the subject or headspace from a stool sample from the subject, wherein the VOCs are selected from the group consisting of ethyl acetate, acetic acid, 4-methyl-1-pentanol, and 2,6-dimethylnonane; and diagnosing a subject as having a CDI when there are one, two, three, or all four of the VOCs present in the sample.

In some embodiments, the methods include detecting the presence in the sample of one, two or three VOCs selected from the group consisting of ethyl acetate, acetic acid, and 4-methyl-1-pentanol; and diagnosing a subject who has one, two or all three of ethyl acetate, acetic acid, and 4-methyl-1-pentanol in the sample as having a CDI. The methods can include detecting any subcombination of the four metabolites, e.g., ethyl acetate and acetic acid; 4-methyl-1-pentanol and 2,6-dimethylnonane; ethyl acetate and 4-methyl-1-pentanol; acetic acid and 2,6-dimethylnonane; ethyl acetate, acetic acid, and 4-methyl-1-pentanol; ethyl acetate, acetic acid, and 2,6-dimethylnonane; acetic acid, 4-methyl-1-pentanol, and 2,6-dimethylnonane; ethyl acetate, 4-methyl-1-pentanol, and 2,6-dimethylnonane; and diagnosing a subject as having a CDI when there are one or more of the VOCs present in the sample.

In some embodiments, the subject has diarrhea, and the method includes diagnosing the subject with CDAD.

Also provided herein are methods for treating a subject who has a *Clostridium difficile* infection (CDI), e.g., *C. difficile*-Associated Diarrhea (CDAD). The methods include obtaining a sample comprising ambient air from near a subject or headspace from a stool sample from a subject, e.g., a subject suspected of have a *C. difficile* infection; detecting the presence in the sample of one, two, three, or all four VOCs selected from the group consisting of ethyl acetate, acetic acid, 4-methyl-1-pentanol, and 2,6-dimethylnonane; and administering a treatment to a subject who has one, two, three, or all four of the VOCs in the ambient air.

In addition, provided herein are methods for monitoring efficacy of a treatment for a *Clostridium difficile* infection (CDI), e.g., *C. difficile*-Associated Diarrhea (CDAD), in a subject, e.g., a subject suspected of have a *C. difficile* infection. The methods include determining a first level of one, two, three, or all four volatile organic compounds (VOCs) produced by the *C. difficile* in a sample comprising ambient air from near the subject or headspace from a stool sample suspected of comprising *C. difficile* isolated from the subject, wherein the VOCs are selected from the group consisting of ethyl acetate, acetic acid, 4-methyl-1-pentanol, and 2,6-dimethylnonane, in the subject; administering a treatment for CDI to the subject; determining a second level of the VOCs in a sample obtained after administration of the treatment to the subject; and comparing the first and second levels of VOCs, wherein a decrease in the VOCs indicates that the treatment has been effective in treating the CDI in the subject, and an increase or no change indicates that the treatment has not been effective in treating the CDI in the subject.

In some embodiments, the treatment comprises administration of one or more doses of one or more antibiotic compounds, e.g., metronidazole, vancomycin, fidaxomicin, or rifaximin.

In some embodiments, the treatment comprises non-antibiotic therapy, e.g., fecal bacteriotherapy, probiotics, or monoclonal antibodies.

Also provided herein are methods of identifying a candidate compound for the treatment of *Clostridium difficile* infection (CDI), e.g., *C. difficile*-Associated Diarrhea (CDAD). The methods include providing a test sample comprising *C. difficile*; detecting a baseline level of VOCs in the headspace of the sample in the absence of the test compound, wherein the VOCs are selected from the group consisting of ethyl acetate, acetic acid, 4-methyl-1-pentanol, and 2,6-dimethylnonane in the subject; contacting the test sample with a test compound; determining a second level of the VOCs in a the test sample; comparing the second level of VOCs to the baseline level; and identifying a test compound that decreases levels of VOCs in the test sample as a candidate compound for the treatment of CDI, e.g., for CDAD.

Further provided herein are methods for detecting the presence of a *C. difficile* bacteria or infection in a sample. The methods include obtaining gas from the headspace of the sample; determining the presence of one, two, three, or all four of the VOCs selected from the group consisting of ethyl acetate, acetic acid, 4-methyl-1-pentanol, and 2,6-dimethylnonane in the sample, wherein the presence of one, two, three, or all four of ethyl acetate, acetic acid, 4-methyl-1-pentanol, and 2,6-dimethylnonane indicates the presence of *C. difficile* in the sample.

The methods described herein can include detecting any subcombination of the four metabolites, e.g., ethyl acetate and acetic acid; 4-methyl-1-pentanol and 2,6-dimethylnonane; ethyl acetate and 4-methyl-1-pentanol; acetic acid and 2,6-dimethylnonane; ethyl acetate, acetic acid, and 4-methyl-1-pentanol; ethyl acetate, acetic acid, and 2,6-dimethylnonane; acetic acid, 4-methyl-1-pentanol, and 2,6-dimethylnonane; ethyl acetate, 4-methyl-1-pentanol, and 2,6-dimethylnonane.

In some embodiments, the methods include detecting the presence of ethyl acetate. In some embodiments, the methods include detecting the presence of acetic acid. In some embodiments, the methods include detecting the presence of 4-methyl-1-pentanol. In some embodiments, the methods include detecting the presence of 2,6-dimethylnonane.

In some embodiments, determining the presence of a VOC comprises assaying the sample to detect the presence the VOC. In some embodiments, assaying the sample to detect the presence the VOC comprises using a gas chromatography (GC) or spectrometry method. In some embodiments, the spectrophotometry method is mobility spectrometry (IMS) or differential mobility spectrometry (DMS).

In some embodiments, the sample is from a human, e.g., a human subject suspected of have a *C. difficile* infection. The methods can include selecting the subject on the basis that they are suspected of having a CDI, e.g., CDAD, e.g., on the basis that they have diarrhea.

The methods described herein need not be exclusive and can be used in combination.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 is a representative GC-MS total ion chromatogram of the volatile organic metabolite profile of a stool sample from a patient with CDI. A: ethyl acetate, B: acetic acid, C: 4-methyl-1-pentanol, D: 2,6-dimethylnonane.

DETAILED DESCRIPTION

A critical barrier to reducing the nosocomial spread of CDI is the delay in timely identification of CDI cases, with subsequent delays in initiation of appropriate antimicrobial therapy and implementation of contact precautions and isolation measures to reduce the risk of horizontal CDI transmission (McFarland et al., The New England Journal of Medicine 1989, 320, 204-10; Cohen et al., Infection Control and Hospital Epidemiology 2010, 31, 431-55; McDonald et al., Morbidity and mortality weekly report 2012, 61, 157-62; Wilcox, Clinical Microbiology and Infection 2012, 18 Suppl 6, 13-20; Scheurer, Journal of Hospital Medicine 2008, 3, 156-9). Diagnostic testing for CDI has traditionally been time-consuming and labor-intensive, relying on highly accurate but slow toxigenic culture or cell culture cytotoxicity neutralization assays (CCNA) (Brecher et al., Clinical Infectious Diseases 2013, 57, 1175-81; Crobach et al., Clinical Microbiology and Infection 2009, 15, 1053-66; Chang et al., Infection and Immunity 1978, 22, 418-22). Rapid enzyme immunoassays detecting *C. difficile* glutamate dehydrogenase (GDH), toxin A, and toxin B, and molecular assays targeting the toxin B tcdB gene have been developed over the past decade, and have largely supplanted the use of toxigenic culture or CCNA for clinical diagnosis of patients with CDI (Cohen et al., Infection Control and Hospital Epidemiology 2010, 31, 431-55; Brecher et al., Clinical Infectious Diseases 2013, 57, 1175-81; Crobach et al., Clinical Microbiology and Infection 2009, 15, 1053-66; Surawicz et al., The American Journal of Gastroenterology 2013, 108, 478-98; quiz 499). These rapid assays have their own drawbacks: while toxin immunoassays are relatively inexpensive and easy to perform, they are far less sensitive than CCNA and toxigenic culture, missing as many as 20-50% of true CDI cases, and while GDH antigen assays are relatively sensitive, they are unable to distinguish toxigenic and non-toxigenic *C. difficile* strains (Dubberke et al., Infection Control and Hospital Epidemiology 2014, 35, 628-45; Wilcox, Clinical Microbiology and Infection 2012, 18 Suppl 6, 13-20; Brecher et al., Clinical Infectious Diseases 2013, 57, 1175-81; Crobach et al., Clinical Microbiology and Infection 2009, 15, 1053-66; Longtin et al., Clinical Infectious Diseases 2013, 56, 67-73; Peterson et al., American Journal of Clinical Pathology 2011, 136, 372-80). While nucleic acid amplification testing (NAAT) for tcdB is extremely sensitive for the detection of toxin-producing *C. difficile* in the specimen, testing is relatively costly, and a positive assay may reflect asymptomatic carriage of strains with toxin genes rather than active production of toxin and clinical disease (Dubberke et al., Infection Control and Hospital Epidemiology 2014, 35, 628-45; Wilcox, Clinical Microbiology and Infection 2012, 18 Suppl 6, 13-20; Surawicz et al., The American Journal of Gastroenterology 2013, 108, 478-98; quiz 499; Longtin et al., Clinical Infectious Diseases 2013, 56, 67-73; Eastwood et al., Journal of Clinical Microbiology 2009, 47, 3211-7; Novak-Weekly et al., Journal of Clinical Microbiology 2010, 48, 889-93). Several multistep diagnostic algorithms have been developed to overcome the diagnostic performance limitations of each individual CDI test, most using an initial GDH antigen screening assay followed by either a CCNA, NAAT, or toxin enzyme immunoassay (Cohen et al., Infection Control and Hospital Epidemiology 2010, 31, 431-55; Brecher et al., Clinical Infectious Diseases 2013, 57, 1175-81; Crobach et al., Clinical Microbiology and Infection 2009, 15, 1053-66; Barbut et al., Clinical Microbiology and Infection 2014, 20, 136-44; Ticehurst et al., Journal of Clinical Microbiology 2006, 44, 1145-9; Fenner et al., Journal of Clinical Microbiology 2008, 46, 328-30; Reller et al., Journal of Clinical Microbiology 2007, 45, 3601-5; Grein et al., Clinical Microbiology and Infection 2014, 20, 65-9; Schroeder et al., Journal of Clinical Microbiology 2014, 52, 489-96.

Despite these advances in rapid stool testing, there are delays of 2-5 days between the onset of clinical symptoms and stool sampling, and another 0.5-3.5 days between sample collection and actionable test results (Scheurer, Journal of Hospital Medicine 2008, 3, 156-9; Barbut et al., Clinical Microbiology and Infection 2014, 20, 136-44; Frenz and McIntyre, QJM 2003, 96, 579-582; Kundrapu et al., Journal of Clinical Microbiology 2013, 51, 2365-70; Sunkesula et al., Clinical Infectious Diseases 2013, 57, 494-500). The lag between the onset of symptoms and sampling is multifactorial, attributed to a lack of clinical suspicion for CDI until patients develop persistent, clinically significant diarrhea, lack of communication between the ordering clinician and the nurse caring for the patient, the frequency of the patient physically leaving their inpatient room for testing or procedures, waiting for the patient to produce a stool sample and collect the specimen in an appropriate container, and a lack of conveniently accessible collection materials for the stool sample (Scheurer, Journal of Hospital Medicine 2008, 3, 156-9; Kundrapu et al., Journal of Clinical Microbiology 2013, 51, 2365-70; Sunkesula et al., Clinical Infectious Diseases 2013, 57, 494-500). Factors contributing to a delay between submission of a stool sample to the clinical microbiology laboratory and CDI test results include rejection of stool specimens due to leakage or improper labeling, batching of samples in the laboratory for more efficient processing, and the time it takes to run the CDI assay or multistep diagnostic algorithm itself (Barbut et al., Clinical Microbiology and Infection 2014, 20, 136-44; Kundrapu et al., Journal of Clinical Microbiology 2013, 51, 2365-70). Anticipating a delay in obtaining test results, many providers prescribe CDI antimicrobial therapy empirically until test results return, resulting in frequent, unnecessary treatment of patients who ultimately test negative for CDI (Kundrapu et al., Journal of Clinical Microbiology 2013, 51, 2365-70; Sunkesula et al., Clinical Infectious Diseases 2013, 57, 494-500).

There is an unmet need for diagnostic methods that will reduce this interval between onset of clinical symptoms and laboratory diagnosis of CDI. Described herein is a novel approach to the diagnosis of CDI based on the detection of volatile metabolites of the *C. difficile* microbiome in stool samples from patients with CDI and in air samples from their environment. We have identified a volatile metabolite signature of CDI that can be used for bedside identification of patients with CDI, allowing prompt antimicrobial treatment of patients with CDI, withholding of empiric antimicrobials in patients without CDI, and initiation of contact precaution and isolation measures to reduce the nosocomial spread of CDI.

The Unique Microbiome and Metabolome of CDI.

Disruption of the normal gastrointestinal flora by antibiotics predisposes individuals to CDI, creating an environment that promotes *C. difficile* spore germination, vegetative proliferation, and toxin release. The normal human intestinal microbiome is a complex and highly diverse ecosystem of trillions of cells, dominated by Firmicutes (including *Lactobacillus, Clostridium, Eubacterium, Leuconostoc*, and *Bacillus* spp.) and Bacteroidetes (including *Bacteroides* and *Porphyromonas* spp.), with minority populations of Proteobacteria, Actinobacteria, Spirochaetes, Lentisphaerae, and Tenericutes (Bäckhed et al., Science 2005, 307, 1915-20; Eckburg et al., Science 2005, 308, 1635-8; Rea et al., Proceedings of the National Academy of Sciences of the United States of America 2011, 108 Suppl, 4639-44; Huttenhower et al., Nature 2012, 486, 207-214). While there is heterogeneity in the composition of taxa in the intestinal microbiota, metagenomic carriage of metabolic pathways between individuals is relatively stable (Huttenhower et al., Nature 2012, 486, 207-214; Franzosa et al., Proceedings of the National Academy of Sciences of the United States of America 2014, 111, E2329-38). This commensal microbial community and its metabolic networks play a key role in training host innate immunity and in nutrient metabolism, maintaining an environment that promotes enteric pathogen resistance (Bäckhed et al., Science 2005, 307, 1915-20; Eckburg et al., Science 2005, 308, 1635-8; Huttenhower et al., Nature 2012, 486, 207-214 Gill et al., Science 2006, 312, 1355-9; Chang et al., The Journal of Infectious Diseases 2008, 197, 435-8). This microbiome-mediated resistance to colonization and infection by enteric pathogens is both indirect, in the stimulation of host production of antimicrobial peptides, inflammatory cytokines, and mucosal IgA, and direct, in competitive consumption of nutrients, production of bacteriocins, and secretion of organic acids and antimicrobial peptides that impair the adhesion of these pathogens to enterocytes (Seekatz and Young, The Journal of Clinical Investigation 2014, 124(10):4182-9; Buffie and Pamer, Nature Reviews Immunology 2013, 13, 790-801; Fukuda et al., Nature 2011, 469, 543-7; Fukuda et al., Gut Microbes 2012, 3, 449-54.).

Antibiotic exposure disrupts the structure and function of this complex microbial community, decimating its diversity and shifting the intraluminal metabolic environment to favor the proliferation of enteric pathobionts. Exposure to antibiotics such as ciprofloxacin, clindamycin, cephalosporins, or metronidazole alters the community structure of the intestinal microbiome for several weeks to months, with particular depletion of Firmicutes and Bacteroidetes and proliferation of other microbes such as Proteobacteria and Enterococcaceae (Seekatz and Young, The Journal of Clinical Investigation 2014, 124(10):4182-9; Rea et al., Proceedings of the National Academy of Sciences of the United States of America 2011, 108 Suppl, 4639-44; Buffie et al., Infection and Immunity 2012, 80, 62-73; Dethlefsen et al., PLoS Biology 2008, 6, e280; Peterfreund et al., PLoS One 2012, 7, e46966; Vincent et al., Microbiome 2013, 1, 18. Lysis of bacterial cells frees ecologic niches, reduces competition for limited resources, and results in a nutritional environment with abundant sugar alcohols, primary bile acids such as taurocholine, and sialic acids liberated from host mucins (Britton and Young, Gastroenterology 2014, 146, 1547-53; Ng et al., Nature 2013, 502, 96-9; Stiemsma et al., Cell Research 2014, 24, 5-6; Theriot et al., Nature Communications 2014, 5, 3114; Song et al., PLoS One 2013, 8, e81330; Wilson and Perini, Infection and Immunity 1988, 56, 2610-4).

*C. difficile* thrives in this altered metabolic milieu. Taurocholine promotes germination of *C. difficile* spores, and the vegetative forms catabolize sialic acid and other liberated carbon sources, proliferating to high levels in the colon and releasing exotoxins as they reach their stationary phase and deplete existing carbon sources (Seekatz and Young, The Journal of Clinical Investigation 2014, 124(10):4182-9; Dupuy and Sonenshein, Molecular Microbiology 1998, 27, 107-20; Ng et al., Nature 2013, 502, 96-9; Howerton et al., The Journal of Infectious Diseases 2013, 207, 1498-504). The fecal microbiota of patients with CDI remains limited in its diversity, with persistent loss of butyrate-producing Clostridiales families such as Lachnospiraceae and Ruminococcaceae and an increase in acetate and lactic acid-producing flora (Chang et al., Journal of Infectious Diseases 2008, 197, 435-8; Peterfreund et al., PLoS One 2012, 7, e46966; Song et al., PLoS One 2013, 8, e81330; Antharam et al., Journal of Clinical Microbiology 2013, 51, 2884-92; Skraban et al., PloS One 2013, 8, e58005; Schubert et al., mBio 2014, 5, e01021-14).

The Distinctive 'Scent' of the CDI Microbiome.

The transformed CDI microbiome, intestinal epithelial damage, and host immune response results in a distinctive, potent odor in the stool and environment of patients with CDI (Bartlett and Gerding, Clinical Infectious Diseases 2008, 46 Suppl 1, S12-8; Burdette and Bernstein, Clinical Infectious Diseases 2007, 44, 1142). Nurses have been able to identify stool specimens from patients with CDI with a sensitivity of 55-84% and specificity of 77-83% based on this distinctive smell, although another study in which nurses were fully blinded to patient and stool characteristics reported a sensitivity of only 26% and specificity of 69% (Burdette and Bernstein, Clinical Infectious Diseases 2007, 44, 1142; Johansen et al., Age and Ageing 2002, 31, 487-8; Rao et al., Clinical Infectious Diseases 2013, 56, 615-6). A dog, with its olfactory limit of detection in the low parts-per-trillion range, has been trained to recognize stool samples from patients with CDI with 100% sensitivity and specificity, and to identify patients with CDI by walking by each patient's hospital bed and detecting this distinctive aroma with 83-86% sensitivity and 97-98% specificity in both CDI outbreak and non-outbreak settings (Bomers et al., BMJ 2012, 345, e7396; Bomers et al., The Journal of Infection 2014, 69(5):456-61). As noted by the authors of these studies, however, the dog required intensive, specialized training procedures, they did not identify what odorants the dog was actually detecting, a substantial proportion of their non-CDI controls were patients without any diarrhea, and confounding may have been introduced by the fact that all CDI patients were in special isolation rooms and control patients in regular ward rooms (Bomers et al., BMJ 2012, 345, e7396). In a small study of stool samples from patients with various causes of infectious diarrhea, including 6 patients with CDI, 5 with Campylobacter, 5 with rotavirus, 5 with adenovirus, and 3 with giardiasis, samples from each group had a distinct global volatile organic compound profile, with a predominance of furans in patients with CDI (Probert et al., Gut 2004, 53, 58-61). In a subsequent study, the same group of investigators were able to predict membership in asymptomatic, ulcerative colitis, Campylobacter jejuni, and CDI patient groups based on differences in the global volatile organic compound profile of stored stool samples, although the number of patients with CDI was limited and the volatile components characteristic of patients with CDI were not specifically identified (Garner et al., FASEB J 2007, 21, 1675-1688).

Samples

The methods described herein can be performed on a gas or liquid sample. In some embodiments, the sample is ambient air from near (within 0-12 or 1-10 or 2-6 inches) an individual or their bathroom. Alternatively, the methods can be performed using headspace from a stool sample known or suspected to include *C. difficile*, e.g., commercially-available or lab-cultured samples, or primary samples from a subject, e.g., a clinical stool sample.

In certain embodiments, the invention involves taking a clinical sample from a subject. The *C. difficile*, if present, in the sample, produce distinctive VOCs. The VOCs can be collected and analyzed using a method described herein or known in the art, see, e.g., US20100291617. In some embodiments, the sample is a gas, e.g., ambient air from near a patient or in a patient's bathroom, or gas from the headspace of a stool sample. Where headspace gas from a stool sample is used, the gas should be collected after the sample has emitted gases into the headspace for a sufficient amount of time for the compounds to be present, e.g., at least 1 minute, e.g., 1-2, 1-3, 1-4, 1-5, 1-6, 1-7, 1-8, 1-9, or 1-10 minutes, preferably in an air-tight, sealed environment, but in a short period of time after the fresh sample is provided, e.g., within 1-2 hours of provision of the sample.

Detection Methods

A number of methods known in the art can be used to detect the presence of the VOCs described herein in a sample. Exemplary methods (particularly for use with a gas sample) include gas chromatography (GC); spectrometry, for example mass spectrometry (including quadrapole, time of flight, tandem mass spectrometry, ion cyclotron resonance, and/or sector (magnetic and/or electrostatic)), ion mobility spectrometry, field asymmetric ion mobility spectrometry, and/or DMS; fuel cell electrodes; light absorption spectroscopy; nanoparticle technology; flexural plate wave (FPW) sensors; electrochemical sensors; photoacoustic equipment; laser-based equipment; electronic noses (bio-derived, surface coated); and various ionization techniques. See, e.g., US20100291617 and US20070003996. Preferred methods include ion mobility spectrometry (IMS) or differential mobility spectrometry (DMS).

In some embodiments, the methods described herein include the use of differential mobility spectrometry to detect VOCs in a sample. An exemplary micro-machined differential mobility spectrometer (DMS), developed for chemical and biological sensing applications, is currently available from Sionex Corporation. DMS has several features that make it an excellent platform for VOC analysis: it is quantitative, selective, and exquisitely sensitive, with a volatile detection limit in the parts-per-trillion range (Davis et al., In: 12th International Conference on Transducers, Solid-State Sensors, Actuators and Microsystems; 2003; p. 1233-8 vol. 2; Miller et al., In: Solid-State Sensors and Actuators Workshop; 2000; Hilton Head, S.C.; 2000; Krebs et al., Sensors Journal, IEEE 2005; 5(4):696-703). Unlike mass spectrometry, which separates particles based on mass/charge ratios, DMS harnesses differences in ion mobility in low and high electric fields to achieve a gas-phase separation of ions at atmospheric pressure. DMS rapidly detects compounds that are difficult to resolve by other analytical techniques such as mass spectrometry in challenging matrices such as human breath (Kanu et al., J Mass Spectrom 2008; 43:1-22; Kanu et al., J Chromatogr A 2008; 1177:12-27; Luong J et al., J Chromatogr Sci 2006; 44:276-286; Nazarov et al., Anal Chem 2006; 7697-706; Kolakowski et al., Analyst 2007; 132:842-64).

DMS can be tuned to monitor specific ion masses, thus tailoring response characteristics to focus on various compounds of interest. It requires no reagents, generates the high fields required by the sensor using a small power supply, and has already been microfabricated, resulting in a small, portable machine that can be used at the bedside, with a turnaround time of several minutes. DMS has been used successfully in several commercial settings, including a hand-held, portable detector of trace levels of chemical warfare agents from General Dynamics (JUNO™) and airport explosives detectors from Thermo (see, e.g., U.S. Pat. No. 7,605,367). DMS technology has also been successfully applied to the characterization of unique VOCs produced by Mycobacterium tuberculosis and other bacteria (Fong et al., Anal Chem 2011; 83:1537-46; Shnayderman et al., Anal Chem 2005; 77:5930-7).

To perform a measurement using a DMS, a gas sample is introduced into the spectrometer, where it is ionized, and the ions are transported through an ion filter towards the detecting electrodes (Faraday plates) by a carrier gas. The DMS device can separate chemical components of a substance based on differing ion mobilities. For other devices, measurements are performed using methods known in the art.

Additional non-limiting examples of systems that can be used in the present methods include those described in US20090078865; US20130168548; US20100291617 and US20070003996.

In some embodiments, the methods include obtaining a sample of ambient air and detecting the presence and/or levels of VOCs in the air, to provide a reference for subtraction of ambient VOCs.

A number of methods are known in the art for detecting the presence and/or levels of the VOCs in a liquid sample, including but not limited to chromatography (e.g., HPLC) and spectrophotometry (e.g., MS, LC-MS, MALDI-TOF, and other of the methods described above for gas-phase samples).

Combination Diagnostics

In some embodiments, the methods include performing an additional diagnostic test for CDI, e.g., for CDAD. A number of such tests are known in the art and include stool tests for *C. difficile* toxins or toxigenic (*C. difficile*, e.g., rapid or enzyme immunoassay for *C. difficile* glutamate dehydrogenase (GDH), and toxins A/B, or NAAT for *C. difficile* toxin B gene sequences (see, e.g., Brecher et al., Clinical Infectious Diseases 2013, 57, 1175-81; Crobach et al., Clinical Microbiology and Infection 2009, 15, 1053-66; Surawicz et al., The American Journal of Gastroenterology 2013, 108, 478-98), or colonoscopic or histopathologic findings revealing pseudomembranous colitis. See, e.g., Cohen et al., Infect Control Hosp Epidemiol 2010; 31(5): 431-455.

Methods of Treatment

The methods described herein can be used to select a treatment for a subject, and can optionally include administering the treatment to a subject. When a subject has been diagnosed by a method described herein as having CDI, e.g., CDAD, then a treatment for CDI, e.g., CDAD can be administered.

A number of antibiotic compounds are known in the art for use in subjects with CDI, e.g., CDAD, including metronidazole, vancomycin, fidaxomicin, or rifaximin. Non-antibiotic therapy, e.g., fecal bacteriotherapy, probiotics, or monoclonal antibodies, can also be used in addition to or as an alternative to an antibiotic. Colectomy can be considered for severely ill patients. See, e.g., Cohen et al., Infect Control Hosp Epidemiol 2010; 31(5):431-455.

Monitoring Treatment Efficacy

As described herein, successful treatment of a *C. difficile* infection is expected to result in a decrease in specific VOCs. Thus, the methods can include repeated assays of VOC levels in a subject, e.g., before, during, and after administration of a treatment for CDI, e.g., for CDAD. A decrease in VOC levels would indicate that the treatment has been successful. In some embodiments, levels of one, two, three or all four of ethyl acetate, acetic acid, 4-methyl-1-pentanol, and 2,6-dimethylnonane are determined.

Methods of Identifying Novel Therapeutic Agents

Included herein are methods for screening test compounds, e.g., polypeptides, polynucleotides, inorganic or organic large or small molecule test compounds, to identify agents useful in the treatment of CDI, e.g., of CDAD.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample comprising *C. difficile*, and the ability of the test compound to decrease levels of a VOC as described herein in the headspace of the sample is determined.

In some embodiments, the test sample is, or is derived from (e.g., a sample taken from) an in vivo model of a disorder as described herein. For example, an animal model, e.g., a rodent (such as a hamster, rat or mouse) or a pig, which has been infected with *C. difficile* can be used. Animal models of *C. difficile* infection are described in Hutton et al., FEMS Microbiol Lett. 2014 March; 352(2):140-9.

A test compound that has been screened by a method described herein and determined to decrease VOCs, can be considered a candidate compound. A candidate compound that has been screened, e.g., in an in vivo model of a disorder, e.g., a rodent infected with *C. difficile*, and determined to decrease VOCs in a sample comprising ambient air from the infected animal model or headspace from a stool sample from the infected animal model, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that decrease *C. difficile*-associated VOCs in an animal model) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating a CDI, e.g., CDAD. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a CDI, e.g., CDAD, e.g., as described in Hutton et al., FEMS Microbiol Lett. 2014 March; 352(2):140-9. The animal can be monitored for a change in the disorder, e.g., for an improvement in a parameter of the disorder, e.g., a parameter related to clinical outcome. In some embodiments, the parameter is VOCs or survival, and an improvement would be a reduction in VOCs or an increase in survival. In some embodiments, the subject is a human, e.g., a human with a CDI, e.g., CDAD, and the parameter is levels of *C. difficile* VOCs or survival.

EXAMPLES

The invention is further described in the following examples, which do not limit the scope of the invention described in the claims.

Example 1. VOC Profiling of CDAD Patient Stool Samples

To determine a stool VOC profile characteristic of patients with CDAD, we collected fresh stool specimens from 69 patients with suspected CDAD sent to our microbiology laboratory for CDAD testing from November/2013-February/2014 and adsorbed the headspace gas of each sample onto sorbent traps designed to retain volatile organic analytes of diverse boiling points (C2-C30) and polarity, and used thermal desorption gas chromatography-mass spectrometry (GC-MS) for delineation of each component of the volatile metabolome in these stool samples. Stool specimens were tested by rapid membrane immunoassay for *C. difficile* glutamate dehydrogenase antigen and toxins A/B, and specimens with indeterminate toxin results were tested by PCR for toxin B gene sequences. Specimens that were antigen and toxin-positive or antigen and toxin PCR-positive were considered true positives for this analysis.

Of the 69 patients, median age was 58 years (IQR 49, 68), 27 (39%) were female, 44 (64%) had an underlying malignancy, 24 (35%) were exposed to proton pump inhibitors and 13 (19%) to corticosteroids. 24 patients were diagnosed with CDAD (9 antigen and toxin-positive, 15 antigen and toxin PCR-positive); 45 patients did not have CDAD.

A representative GC-MS total ion chromatogram of the volatile organic metabolite profile of a stool sample from a patient with CDI is shown in FIG. 1. The volatile metabolite profile of each stool sample contained a complex bouquet of aldehydes, ketones, esters, furans, alcohols, and sulfur and nitrogen-containing compounds. Using LASSO and elastic net-regularized logistic models with 5-fold cross-validation (Tibshirani, Journal of the Royal Statistical Society: Series B (Methodological) 1996, 58, 267-288; Hastie, *The Elements of Statistical Learning, Second Edition: Data Mining, Inference, and Prediction;* 2nd ed.; Springer: New York, 2009), we determined a parsimonious set of volatile organic metabolites—ethyl acetate, acetic acid, 4-methyl-1-pentanol, and 2,6-dimethylnonane—that discriminated stool samples from patients with CDI versus diarrhea due to other causes with an area under the receiver-operating characteristic curve (ROC AUC) of 0.80.

We identified 589 distinct volatile metabolites in all 69 stool samples, with a median of 87 VOCs (range 43, 155) VOCs per patient, with a complex mixture of aldehydes, ketones, esters, alcohols, furans, and sulfur and nitrogen-containing compounds. LASSO and elastic net approaches both identified a VOC profile of ethyl acetate, acetic acid, 4-methyl-1-pentanol, and 2,6-dimethylnonane in patients with CDAD that distinguished them from patients without CDAD, with an ROC AUC of 0.80.

Example 2. VOC Profiling of CDAD Patient Ambient Air Samples

To determine whether the same methods could be used without waiting for a patient to produce a stool sample, ambient air very close to the patient (about 2-6" away) and the air in their bathroom was assayed.

The air was collected with a sampling pump calibrated to 900 mL/min over a 4 minute period. The volatiles were adsorbed and concentrated onto two Tenax TA/Carbograph 1TD/Carboxen 1003 thermal desorption tubes per sample, so each individual air sample analyzed consisted of about 1.8 L of room air, concentrated.

Air sample data from 3 *C. difficile* cases and 3 controls with other causes of diarrhea is shown below in Table 1. The results demonstrated that ethyl acetate, acetic acid, 4-methyl-1-pentanol, and 2,6-dimethylnonane was present in the room air of patients with confirmed *C. difficile* and mostly absent in the control samples.

TABLE 1

|  | Controls | Cases |
| --- | --- | --- |
| Ethyl acetate | 0/3 | 3/3 |
| Acetic acid | 1/3 | 3/3 |
| 4-methyl-1-pentanol | 0/3 | 3/3 |
| 2,6-dimethylnonane | 1/3 | 2/3 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for diagnosing a subject with a *Clostridium difficile* infection (CDI), the method comprising:
    obtaining a gas sample comprising ambient air obtained from within 12 inches of a subject or headspace of a sealed container containing a stool sample suspected of comprising *C. difficile* isolated from a subject;
    detecting the presence in the sample of volatile organic compounds (VOCs) produced by the *C. difficile* in a sample comprising ambient air from near the subject or headspace of a sealed container containing a stool sample suspected of comprising *C. difficile* isolated from the subject, wherein the VOCs comprise acetic acid and 4-methyl-1-pentanol; and
    diagnosing a subject as having a CDI when both of the VOCs are present in the gas sample.

2. The method of claim 1, wherein the subject has diarrhea, and the method includes diagnosing the subject with *Clostridium difficile* Associated Diarrhea (CDAD).

3. The method of claim 1, further comprising:
    administering a treatment for a CDI to a subject who has both of the VOCs in the ambient air.

4. A method of monitoring efficacy of a treatment for a *Clostridium difficile* infection (CDI), in a subject, the method comprising:
    determining a first level of volatile organic compounds (VOCs) produced by the *C. difficile* in a first gas sample comprising ambient air from within 12 inches of the subject or headspace of a sealed container containing a stool sample suspected of comprising *C. difficile* isolated from the subject, wherein the VOCs comprise acetic acid and 4-methyl-1-pentanol, in the subject;
    administering a treatment for a CDI to the subject;
    determining a second level of the VOCs in a subsequent gas sample of the same type as the first sample obtained after administration of the treatment to the subject; and
    comparing the first and second levels of VOCs, wherein a decrease in the VOCs indicates that the treatment has been effective in treating the CDI in the subject, and an increase or no change indicates that the treatment has not been effective in treating the CDI in the subject.

5. The method of claim 3, wherein the treatment comprises administration of one or more doses of one or more antibiotic compounds that are used to treat subjects with CDI.

6. The method of claim 5, wherein the antibiotic compound is metronidazole, vancomycin, fidaxomicin, or rifaximin.

7. The method of claim 3, wherein the treatment comprises a non-antibiotic therapy that is used to treat subjects with CDI.

8. The method of claim 7, wherein the non-antibiotic therapy comprises fecal bacteriotherapy or probiotics.

9. A method comprising:
    obtaining gas from the headspace of a sealed container containing a stool sample;
    determining the presence of volatile organic compounds (VOCs) comprising acetic acid and 4-methyl-1-pentanol in the gas.

10. The method of claim 1, further comprising detecting the presence of ethyl acetate.

11. The method of claim 1, further comprising detecting the presence of 2,6-dimethylnonane.

12. The method of claim 1, wherein determining the presence of a VOC comprises assaying the sample to detect the presence of the VOC.

13. The method of claim 12, wherein assaying the sample to detect the presence the VOC comprises using a gas chromatography (GC) or spectrometry method.

14. The method of claim 13, wherein the spectrophotometry method is mobility spectrometry (IMS) or differential mobility spectrometry (DMS).

15. The method of claim 1, wherein the sample is from a human.

16. The method of claim 3, wherein the subject has diarrhea, and the method includes diagnosing the subject with *C. difficile* Associated Diarrhea (CDAD) and administering a treatment for CDAD to the subject.

\* \* \* \* \*